United States Patent [19]
Dos Santos

[11] Patent Number: 5,972,340
[45] Date of Patent: Oct. 26, 1999

[54] SLIMMING CREAM BASED ON PLANTS

[76] Inventor: Georgina Dos Santos, Rua do Zambujal, 10-4° Esq., Mem Martins P-2725, Portugal

[21] Appl. No.: 09/011,319
[22] PCT Filed: May 31, 1996
[86] PCT No.: PCT/PT96/00004
 § 371 Date: Jul. 10, 1998
 § 102(e) Date: Jul. 10, 1998
[87] PCT Pub. No.: WO97/45100
 PCT Pub. Date: Dec. 4, 1997
[51] Int. Cl.$^6$ ..................................................... A61K 35/78
[52] U.S. Cl. ............................................................ 424/195.1
[58] Field of Search ........................................... 424/195.1

[56] References Cited

U.S. PATENT DOCUMENTS 5,053,433  10/1991  Philippossian et al. ................. 514/909
5,436,230  7/1995  Soudant et al. ............................ 514/21
5,614,215  3/1997  Ribier et al. .............................. 424/450

OTHER PUBLICATIONS

Derwent Abstract of FR 2,406,448, Jun. 1979.
Derwent Abstract of GB 2166954A, May 1986.

*Primary Examiner*—Raymond Henley, III
*Attorney, Agent, or Firm*—Locke Reynolds

[57] ABSTRACT

The present invention refers to a slimming cream based on plants, comprising 0.5 to 5% seaweeds, 0.8 to 8% creeping ivy, 0.3 to 3% horsetail, 0.5 to 5% fenugreek, 0.5 to 5% mallows, 0.3 to 3% witch hazel, 0.4 to 4% wheatgerm oil, 0.2 to 2% camphor, a preservative and an excipient in a sufficient amount to make up a 100%. Another aim of the invention is a process for preparing said cream as well as a method of applying same. The cream according to the present invention is used to promote local slimming and to fight cellulite.

10 Claims, No Drawings

SLIMMING CREAM BASED ON PLANTS

This application is a 371 of PCT/PT96/00004 filed May 31, 1996.

FIELD OF THE INVENTION

The present invention refers to a slimming cream based on plants. It belongs therefore to the vast field of application of compositions based on plant extracts which are used in the treatment of diseases or in locally applied beauty treatments. These extracts act by means of the so-called aromatherapy or balsamtherapy.

BACKGROUND TO THE INVENTION

Plants and Health

Plants, animals and minerals have been used throughout history by human civilizations to produce healing drubs. Written records, such as the ancient Egyptian hieroglyphs, the Bible or Chinese physiotherapy manuals describe the extensive use of natural products for medicinal ends, with Nature still being the most important source of medicines in the whole world.

The World Health Organization has estimated that at least 80% of the world population relies mainly, if not totally, on natural medicinal products. Even in industrialized countries, more than 40% of all pharmaceutical drugs originate from natural sources. Many of these medicines are made with natural ingredients and others are synthetic copies or artificially modified forms of natural chemical products.

In industrialized societies, drugs made from natural sources are increasing in popularity, not as the implementation of a "new fashion", but as the reappearance of an ancient and universal practice, thus opposing the recent competition carried out by the pharmaceutical industry. Allopathic medicine became dependent on man-made chemical products only during the last century. These modern drugs had a great impact on infectious diseases during the 1940s and 1950s, but they did not cure common diseases such as breast, lung and bowel cancer, heart disease, rheumatism or a simple cold. Nonetheless, as far as the effects caused by their frequent use are concerned, the seriousness of such effects has increased.

Evidence that modern drugs are not a remedy for all diseases and that they can harm as well as cure, coincided with an increase in international preoccupation with regard to the depletion and destruction of the world's environment. This apprehension gave rise to a greater awareness of the intricate web of interdependency between living things and also a better understanding of both philosophies concerning the total health of the human being as a whole and natural medicine Man's knowledge of the healing properties of plants, animals and minerals sums tip remarkably the intellectual and cultural evolution of human civilization. A brief consideration of our ignorance of the world is sufficient to make us wonder, as we consider how primitive societies discovered the healing power of the things that surrounded them. Even more extraordinary is the thought of how closely-related plants, for example, were used for the same diseases by communities settled hundreds of miles away from each another, when there is no evidence that they could communicate and therefore exchange their knowledge of the matter.

Although the same drugs may still be used in different parts of the world, they are frequently applied in different ways in the various systems of treatment. Systems such as Chinese traditional medicine or India's aiurvedic medicine differ from allopathic medicine because they treat the person as a whole. These systems explain that health is a state of harmony, or of balance, both inside our body and between each individual and the environment he lives in. Illness is due to a lack of balance and drugs are applied in order to restore such harmony.

Plants furthermore contain the mineral salts that the human body needs for its good functioning and even favor the working of body's glands as far as the secretion of hormones is concerned. We know that hormones play an extremely important role in all vital processes as they regulate the activity of the body's organs and act as faithful guardians of the good functioning thereof Hormones intervene immediately when there is a lack of one substance or an excess of another in the human organism.

We have at our disposal plants with healing properties so that we can keep our metabolism in order (assimilation and disassimilation), detoxicate blood and organic tissues, expel morbid and strange substances and purify and reconstruct our organism.

Health and Beauty

Health and beauty are closely interrelated. Moisturizing milks, nutrient creams and the most sophisticated cosmetics may be used, but if our hormonal and visceral functioning is defective, their beneficial action will be immediately destroyed.

We cannot forget that:

- the digestive system is responsible for the way the skin looks, for the importance of subcutaneous tissues and for the absorption and production of fats;
- the hypophysis is a sort of computer for endocrine secretions which maintains our fragile hormone balance;
- the adrenal glands are responsible, amongst other things, for the pigmentation of the skin;
- a balanced blood formula requires an adequate density of body guardians, that is to say, of blood leucocytes. All the essential extracts used in the present invention multiply the number of leucocytes by means of the well-known process called leucotaxis;
- the sympathetic nervous system regulates our visceral hormones and our appearance;
- the vascular system should be flexible and invigorating;
- the respiratory system Should guarantee perfect oxygenation. All the essential extracts increase said oxygenation, this being the reason why we breathe better in a wood consisting of conifers;
- liver and kidneys are our main purifiers;
- the bowels should defecate perfectly.

All these functions should be balanced, sufficient and invigorating in order to guard against ageing, a process against which the strictly local care of the skin and teguments is of the utmost importance.

SUMMARY OF THE INVENTION

The present invention relates to a composition for local slimming and for fighting cellulitis. Said composition is preferably in the form of a cream based on plant extracts, in particular extracts of seaweeds, creeping ivy, horsetail, fenugreek, mallows and witch hazel, wheatgerm oil, camphor, preservatives and excipients, additionally containing other kinds of fats.

The present invention also relates to a process for preparing said composition and to its local use on the human body in order to fight cellulite and promote a slimming effect.

DETAILED DESCRIPTION OF THE INVENTION

Slimming Composition

A first object of the present invention is a composition for local slimming and for fighting cellulite. As already mentioned above, said composition is usually in the form of a cream based on plant extracts used for local application. The composition consists essentially of seaweeds, creeping ivy, horsetail, fenugreek, mallows and witch hazel, wheatgerm oil, camphor, preservatives and excipients, additionally containing other kinds of fats.

Amongst the useful seaweeds, sea oak (*Fucus vesiculosus*) is especially preferred. Sea oak has been used for many years as a medicine for treating obesity, due to its content of inorganic iodine salts, which have the capacity to absorb fat. The main components are iodine, bromine, mineral salts, amino acids, oligo-elements, vitamins B, C and E and provitamin A. Sea oak has depurative, stimulating and laxative properties. It should be stressed that the natural iodine existing in sea oak plays a valuable role in the human body. Iodine is very important for the internal secretion of malfunctioning glands. Due to the iodine it contains, sea oak stimulates the thyroid gland, which in turn controls the metabolic level of the body, increasing, the synthesis of nucleic acids, glucose, proteins and phospholipids. The oligo-elements, i.e. inorganic substances which are present in small amounts, are indispensable to the organic processes which maintain our general health.

Creeping ivy (*Hedera helix*) has as its main components estrogens and hederin. It has analgesic, antispasmodic and emmenagogic properties.

Horsetail (*Equisetum arvense*) is a very ancient plant, a fossil usually found in seashore deposits. It has been used since ancient Roman times as a vegetable, as animal food and as a medicinal plant. It is very effective for stanching internal as well as external haemorrhages and for reducing swellings, rashes and inflammations. It is also astringent and stimulates immune reaction. The composition thereof contains as active substances alkaloids, saponins, flavonoids, steroids, silicic acid and minerals. It should be stressed that of all its active substances it is silicic acid which forms muscle fibers, tendons and most tissues, such as bronchial tissue, as well as teeth enamel, hair, nose and ear cartilage, the pupil of the eye, blood vessels, the tendons of the abdominal musculature and those joining the spinal column and the bones, etc. Silicium is an essential nutritious element, aimed at successfully fighting skin, kidney and nervous diseases. It helps the body build connective tissue, acting as a cross link between proteoglycans and proteins.

The seeds of fenugreek (*Trigonella foenum-graecum*), also known as Greek hay, contain: mexone, glycides, mannose, trigonelline, choline, fat acids, saponin, proteins and mucilage. The use of fenugreek has been known since olden times. Its seeds, used in poultices, make fat and cellulite disappear. This result is obtained by the presence of a substance which acts on the fat metabolism, a collin which has the capacity to dissolve triglycerides. Mucilage acts favourably because it soothes the irritative state of the mucous membrane. Stomach and intestinal inflammations, even when ulcers are present, are improved with the mucilage of fenugreek, often used in Galenic pharmacy and home medicine as emollients (mucous membrane protectors), laxants, etc.

The components of mallow (*Malva silvestris*) are mucilages and antocyanines, which have relaxing, emollient and laxative properties. It may be used externally in the form of ablutions, poultices and irrigations when the skin is inflamed or congested.

Witch hazel (*Hamamelis Virginiana*), which is actually a common garden plant, was first known by Native American Indians, who used the shoots of the plant to produce divine water and the leaves and skin as a medicine for swellings and tumors. It has been widely used since then in pharmaceutical preparations for treating skin pimples and burns. In fact, the plant is rich in a special kind of tannin, namely hamamelitannin, which is an astringent and vasoconstricting substance and an excellent medicine for the veins as it favours blood circulation. The main active substances contained in the composition of witch hazel are tannins, flavonoids, including quercitrin and camphorol and saponins.

Wheatgerm oil, besides being very rich in vitamin E, also contains other substances having the same texture as the germ itself, namely provitamin A, vitamin F, lecithin and sterols. Vitamin E is extremely valuable. It is a must for our daily health, since it is especially beneficial to the heart and blood. Vitamin E prevents the sudden grouping of the blood platelets and the resulting formation of a viscous mass, in other words, it prevents the blood from coagulating and helps to alleviate a variety of affections such as coronary diseases, diabetes, problems related to menstruation and menopause, ulcers and problems related to old age. This vitamin, which is extraordinarily versatile, also plays a part in our reproductive system, as well as in providing healthy eyesight, and it alleviates bronchial affections, treats serious burns and helps the healing of the skin. Vitamin E improves the general appearance of the skin, helps to cure acne and pimples and gives the skin a healthy appearance. It also helps to maintain a high oxygen level in the blood, favoring blood circulation, and protects the storage of other vitamins in out body. The composition of wheatgerm oil is ideal from the point of view of fat chemistry as it includes a broad spectrum of active substances. The fundamental physiological meaning of vitamin E or of tocopherol (the main active substance of wheatgerm oil) lies in the fact that it is an antioxidant, inhibiting the oxidation processes going on in the body and reducing the quality (or types) of such processes, as well as inhibiting the absorption of oxygen by the body's musculature, in particular in the liver. It furthermore protects against extremely quick oxidative decomposition of the substances which easily oxidate during the course of metabolic processes (e.g. vitamin A). Vitamin E is also involved in controlling the function of the hypophysis and acts on neuro-vegetative centers. The metabolism of hydrocarbons is influenced by it and it acts directly upon the genital field. It favors the formation of capillary vessels and reduces the problems relating to peripheric blood circulation. The phenomena of connective tissue degeneration react positively to vitamin E. When applied by diadermic absorption, vitamin E improves peripheric circulation and strengthens connective tissue. Due to its antioxidant power, vitamin E protects the skin against oxidative disintegration., Camphor, a product of tale camphor-tree (*Cinnamomum camphora*), is a well-tested drug, used in Europe since the XIIth century and widely known from the XVIIth century onwards. Externally used, camphor is a revulsant and internally used, a heart stimulant. The composition of balsams which is used to rub aching muscles includes camphor. It is a stimulant of the heat and nerve centers, an aphrodisiac and antispasmodic drug (reducing muscle tension and spasms).

Among useful preservatives, the following may be pointed out in particular: imidazolinyl-urea, methylparaben, propylparaben, propylene glycol or mixtures thereof.

Preferred excipients are chosen from the group consisting of cetyl alcohol, stearyl alcohol, oleic acid decyl ester, cetyl sulphate, stearyl sulphate, cetyl stearyl sulphate, distilled water and mixtures thereof.

Among the additional fats that may be present in the composition, lanolin and vaseline should be pointed out.

In accordance with a preferred embodiment of the present invention the composition comprises 0.5 to 5% seaweeds, 0.8 to 8% creeping ivy, 0.3 to 3% horsetail, 0.5 to 5% fenugreek, 0.5 to 5% mallows, 0.3 to 3% witch hazel, 0.4 to 4% wheatgerm oil, 0.2 to 2% camphor, a preservative and an excipient of an amount sufficient enough to make up 100%.

In the most preferred embodiment of the present invention the composition comprises 1.95% seaweeds, 3.90% creeping ivy, 0.90% horsetail, 1.95% fenugreek, 1.95% mallows, 0.90% witch hazel, 1.50% wheatgerm oil, 0.60% camphor, a preservative and an excipient of an amount sufficient enough to make up 100%.

Preparation Process

A second object of the present invention is a process for preparing a composition for local slimming and for fighting cellulite, usually in the form of a cream based on plant extracts, meant for local application, as previously mentioned.

The process referred to essentially comprises the following steps:

a) melting the fats at a temperature of about 50 to 90° C.;

b) warming the water or another excipient, or excipient mixture, at the same temperature;

c) adding the component mentioned in b) to the previously melted fats and plant extracts;

d) mixing the ingredients mentioned above; and e) adding the preservative to the mixture obtained in d) at a temperature of 30 to 50° C.

The fats are preferably melted at about 70° C., at which temperature the water is also preferably warmed.

The preservative is added preferably at about 40° C.

Method of Application

A third object of the present invention is a method of application of said composition used for local slimming and for fighting cellulite, usually in the form of a cream.

The cream according to the present invention is introduced into the body by massaging the skill until said slimming cream has been completely absorbed. This simple massage, without the aid of another active cream, helps the circulation of body liquids, dispels obstructions and prevents stagnation.

By means of a powerful bactericide, a healing and regenerating effect on the teguments and mucous membranes, reinforced by an overall effect which depends on its immediate absorption by the skin, the cream according to the present invention acts with the aid of its active components immediately at the level of the cell. These components are scattered throughout the general circulation of the blood in order to attain the target organs they are meant to regenerate, i.e. the liver, heart, nervous system and endocrine glands—which are all vital organs—where said components concentrate according to their individual disposition before they are eliminated, during the time they remain there they stimulate, revive and rejuvenate the target organ.

Thus, some active substances included in the cream according to the present invention act by increasing the secretion of the suprarenal glands, others by decreasing the secretions of the stomach and skin. The healing substances multiply the healing activity several times. Depurative substances increase perspiration (unconscious sweating), gaseous lung exchanges, biliary and pancreatic secretions, as well as the filtering capacity of the kidneys, increasing by one and a half times the excretion and dissolution of triglycerides. The degradation of fats and hydrocarbons produces carbon dioxide which is eliminated by the lungs.

The cream according to the invention was conceived for fighting morbid conditions of our external appearance and figure, such as cellulite, general or local obesity, relaxing or ptosis of the skin and excessive secretion of fat (seborrhoea), which reveal profound bodily dysfunctions and are therefore a favourable field where balsamtherapy or aromatherapy may be successfully applied.

It should be noted that apart from slimming and "rejuvenating" effects, the components of the cream according to the invention contain nutrients which are indispensable to the harmonious balance of the skin and teguments, namely vitamins A, B, C, E, F, oligo-elements, silicium, etc.

Although the present slimming cream contains some of the ingredients present in other creams with the same purpose which may be currently found on the market, it differs from those other creams due to the plants contained in its composition, thus enabling it to act more quickly and not requiring the user to wait at least two weeks, as is usually recommended for the other creams, in order to see the setting in of its effects.

On the other hand, by only using the cream of the invention, good results may be obtained in terns of slimming and of reducing cellulite. The skin becomes toned and fortified and the user feels no need, from an aesthetic point of view, to use another cream as a supplementing thereof.

As already mentioned above, the cream of the present invention is meant for fighting local fat and cellulite, as well as for improving blood circulation by the massaging of the whole body or areas of the body. With regard to local fat, the most active plants are seaweeds, horsetail and also mallows; creeping ivy and fenugreek act particularly on cellulite and witch hazel on the circulation of the blood.

More precisely, the cream according to the invention is applied by massaging the body or areas of the body until it penetrates the skin, if necessary applying a second layer and massaging until it has been absorbed. A massage of about 20 minutes to 2 hours, preferably 45 minutes to 1 hour, over the whole body, is recommended.

The type of massage should be more or less intense, depending on the area to be treated. For instance, in the chest area, the cream should be applied by massaging softly. As already mentioned above, the cream may be applied on the whole body, including the neck and face if necessary.

The periodicity of application varies according to the actual case, varying usually between once a week to 3 times a day, for instance 3 times a week or once a day.

The present invention is illustrated by the following Examples. It should be pointed out, however, that it is not to be limited by the specific details set out therein and thus the Examples are not restrictive as regards the scope of the claims.

EXAMPLES

Example 1

Preparation of a Slimming Cream According to the Invention 200 g of the cream according to the invention are prepared, having the following composition:

| Ingredients | Amounts (g) |
| --- | --- |
| Seaweeds | 3.9 |
| Creeping ivy | 7.8 |
| Horsetail | 1.8 |
| Fenugreek | 3.9 |
| Mallows | 3.9 |
| Witch Hazel | 1.8 |
| Wheatgerm Oil | 3.0 |
| Camphor | 1.2 |
| Preservative | q.s. |
| Excipient q.s. to | 200 g |

Wheatgerm oil was melted at 70°. The excipient was warmed at the same temperature. The warmed excipient was added to the previously melted wheatgerm oil and to the plant extracts. After a thorough mixing of said ingredients the preservative was added to the reaction mixture at a temperature of 40° C.

Example 2

A cream according to the invention was applied during 16 days, once a day on alternate days, on a female individual with the results shown in Table I

TABLE 1

| Place of application | Size (cm) | |
| --- | --- | --- |
| | Before | After |
| Waist | 97 | 80.5 |
| Thigh | 70 | 63.5 |
| Hip | 113 | 106 |

Example 3

The procedure of Example 2 was followed, but during 3 days only, applying the treatment once a day, every day, with the results shown in Table II:

TABLE II

| Place of application | Size (cm) | |
| --- | --- | --- |
| | Before | After |
| Leg | 61 | 58.5 |
| Half-leg | 58.5 | 54 |
| Knee | 48 | 43 |
| Ankle | 38.5 | 36.5 |

Example 4

The procedure of Example 2 was followed, during 1 month and 5 days, every other day, applying the treatment once a day, with the results shown in Table III:

TABLE III

| Place of application | Size (cm) | |
| --- | --- | --- |
| | Before | After |
| Back | 108.5 | 105.5 |
| Hip | 129 | 120 |
| Leg | 78.5 | 74 |
| Knee | 54.5 | 50 |
| Waist | 101.5 | 94 |

Example 5

The procedure of Example 2 was followed, during 1 week, every day, once a day. The male individual who underwent treatment lost 2.5 cm at the waistline and 3 cm at the hipline.

Example 6

The procedure of Example 2 was followed, but the treatment consisted merely of 4 massage sessions during 4 consecutive days. The stomach size of the female individual who underwent treatment decreased from 111 cm to 107 cm.

Example 7

The procedure of Example 2 was followed, but during one and a half months, applying the slimming cream according to the invention once a day, every day, with the results shown in Table IV:

TABLE IV

| Place of application | Size (cm) | |
| --- | --- | --- |
| | Before | After |
| Waist | 78 | 65 |
| Hip | 95 | 86 |
| Leg | 58 | 54 |
| Knee | 42 | 38 |

I claim:

1. Slimming cream based on plants, comprising 0.5 to 5% seaweeds, 0.8 to 8% creeping ivy, 0.3 to 3% horsetail, 0.5 to 5% fenugreek, 0.5 to 5% mallows, 0.3 to 3% witch hazel, 0.4 to 4% wheatgerm oil, 0.2 to 2% camphor, a preservative and an excipient in a sufficient amount to make up 100%.

2. Slimming cream based on plants, comprising 1.95% seaweeds, 3.90% creeping ivy, 0.90% horsetail, 1.95% fenugreek, 1.95% mallows, 0.90% witch hazel, 1.50% wheatgerm oil, 0.60% camphor, a preseivative and an excipient in a sufficient amount to make up 100%.

3. Slimming cream based on plants, according to claim 1 or 2, additionally comprising other fats selected from lanolin and vaseline.

4. Slimming cream based on plants according to claim 1 or 2, wherein the preservative is selected among imidazolinyl-urea, methylparaben, propylparaben, propylene glycol or mixtures thereof.

5. Slimming cream based on plants, according to claim 1 or 2, wherein the excipient is selected from the group consisting of cetyl alcohol, stearyl alcohol, oleic acid decyl ester, cetyl sulphate, stearyl sulphate, cetyl stearyl sulphate, distilled water and mixtures thereof.

6. A process for preparing a slimming cream biased on plants as referred to in claim 1 or 2, essentially comprising the following steps:

a) melting the fats at a temperature of about 50 to 90° C.;

b) warming the excipient, at the same temperature;

c) adding the component mentioned in b) to the previously melted fats and plant extracts;

d) mixing the ingredients referred to above; and e) adding the preservative to the mixture obtained in d) at a temperature of 30 to 50° C.

7. A process according to claim 6, wherein the temperature mentioned in steps a) and b) is about 70° C.

8. A process according to claim 6, wherein the temperature mentioned in step e) is about 40° C.

9. A method for applying the slimming cream according to claim 1 or 2, characterized in that said cream is massaged until it penetrates the skin, if necessary applying a second layer of cream and massaging until it has been completely absorbed.

10. A method according to claim 9, wherein the whole body is massaged from 20 minutes tip to 2 hours, preferably from 45 minutes up to 1 hour, the periodicity of the application being from once a week to 3 times a day, for instance, 3 times a week or once a day.

* * * * *